US012691052B2

(12) United States Patent
Mathias et al.

(10) Patent No.: US 12,691,052 B2
(45) Date of Patent: Jul. 28, 2026

(54) TOPICAL COSMETIC COMPOSITION, USE OF THE COMPOSITION AND SERUM FOR APPLYING ON THE FACE

(71) Applicant: Natura Cosméticos S.A., São Paulo—SP (BR)

(72) Inventors: Michele Helena Mathias, Cajamar—SP (BR); Camila Pereira Santos, Cajamar—SP (BR); Luciana de Miranda Chaves Vasquez Pinto, Cajamar—SP (BR); Silas Arandas Monteiro e Silva, Cajamar—SP (BR); Joice Savietto, Cajamar—SP (BR); Edjane Lima Gusmão, Cajamar—SP (BR); Nicole Gregório Pinto, Cajamar—SP (BR)

(73) Assignee: NATURA COSMÉTICOS S.A., São Paulo —SP (BR)

( * ) Notice: Subject to any disclaimer, the term of this patent is extended or adjusted under 35 U.S.C. 154(b) by 687 days.

(21) Appl. No.: 17/633,378

(22) PCT Filed: Aug. 6, 2019

(86) PCT No.: PCT/BR2019/050320
§ 371 (c)(1),
(2) Date: Feb. 7, 2022

(87) PCT Pub. No.: WO2021/022346
PCT Pub. Date: Feb. 11, 2021

(65) Prior Publication Data
US 2022/0296492 A1     Sep. 22, 2022

(51) Int. Cl.
| | |
|---|---|
| *A61K 8/73* | (2006.01) |
| *A61K 8/06* | (2006.01) |
| *A61K 8/34* | (2006.01) |
| *A61K 8/36* | (2006.01) |
| *A61K 8/365* | (2006.01) |
| *A61K 8/9789* | (2017.01) |
| *A61Q 19/00* | (2006.01) |

(52) U.S. Cl.
CPC ............... *A61K 8/732* (2013.01); *A61K 8/06* (2013.01); *A61K 8/342* (2013.01); *A61K 8/361* (2013.01); *A61K 8/365* (2013.01); *A61K 8/9789* (2017.08); *A61Q 19/008* (2013.01)

(58) Field of Classification Search
None
See application file for complete search history.

(56) References Cited

U.S. PATENT DOCUMENTS

| | | | |
|---|---|---|---|
| 5,958,436 | A | 9/1999 | Hahn et al. |
| 9,956,151 | B2 | 5/2018 | Santhanam et al. |
| 10,123,954 | B1 | 11/2018 | Santhanam et al. |
| 10,981,084 | B2 | 4/2021 | Makerri et al. |

FOREIGN PATENT DOCUMENTS

| | | | | |
|---|---|---|---|---|
| CN | 107405281 A | 11/2017 | | |
| EP | 1604647 B1 | 5/2008 | | |
| FR | 2945209 A1 * | 11/2010 | ............... | A61K 8/60 |
| KR | 10-2018-0082050 A | 10/2018 | | |
| WO | WO 96/19184 A1 | 6/1996 | | |
| WO | WO 2012/083906 A2 | 6/2012 | | |
| WO | WO-2015196392 A1 * | 12/2015 | ............. | A61K 8/062 |
| WO | WO-2018112586 A1 * | 6/2018 | ............... | A61K 8/04 |
| WO | WO 2018/122514 A1 | 7/2018 | | |
| WO | WO 2019/091663 A1 | 5/2019 | | |

OTHER PUBLICATIONS

Machine translation of the Description of WO 2018/112586 A1 (Year: 2024).*
Machine translation of the Description of FR 2945209 (Year: 2024).*
Scharschmidt, T.C., et al., What lives on our skin: ecology, genomics and therapeutic opportunities of the skin microbiome, Drug Discovery Today: Disease Mechanisms vol. 10, No. 3-4 2013 (Year: 2013).*
International Searching Authority, International Search Report and Written Opinion received for International Application No. PCT/BR2019/050320, dated Mar. 30, 2020, 20 pages, National Institute of Industrial Property, Brazil.

* cited by examiner

*Primary Examiner* — H. Sarah Park
(74) *Attorney, Agent, or Firm* — Alston & Bird LLP

(57) ABSTRACT

The present invention is a topical cosmetic composition that helps to reduce and control oiliness of the skin immediately and lastingly, and also to reduce the size of pores, to reduce visual imperfections and to moisturize. The composition helps to maintain a natural healthy microbiota of the skin. The present invention pertains to the field of cosmetic science, and more specifically relates to preparations for treating the skin.

17 Claims, 7 Drawing Sheets

Figure 2. Illustration of the result obtained for research participant no. 08.

TOPICAL COSMETIC COMPOSITION, USE OF THE COMPOSITION AND SERUM FOR APPLYING ON THE FACE

CROSS REFERENCE TO RELATED APPLICATIONS

This application is a national stage application, filed under 35 U.S.C. § 371, of International Application No. PCT/BR2019/050320, filed Aug. 6, 2019, the contents of which are hereby incorporated by reference in their entirety.

FIELD OF THE INVENTION

The present invention describes a topical cosmetic composition that provides immediate and prolonged reduction and control of skin oiliness, as well as pore size reduction, reduction of visual imperfections and moisturization. The present invention is within the field of cosmetic science, more precisely it concerns skin care preparations.

BACKGROUND

Skin or integument is a double layered membrane that covers the entire body surface and is adjacent to mucous membranes that cover the human body orifices. It exhibits great variation in thickness along its entire length, ranging from 1 to 4 mm according to its required biological functions. Among these functions are maintenance of the body integrity by protecting the body against injuries, absorbing and excreting liquids, regulating the body temperature, absorbing ultraviolet rays, metabolizing vitamin D, providing sensory stimuli and cosmetic functions.

The skin can be divided into two parts, the outermost layer being represented by the epidermis and the innermost layer being the dermis which rests on the subcutaneous cellular tissue, which is also part of the skin's structure.

The epidermis is formed by a keratinized stratified squamous epithelium that contains 4 layers: basal, spinous, granular and corneal (horny) layers.

The epidermis cells, in turn, can be divided into 4 groups: stem cells, proliferative cells, differentiated cells and functional cells. The epidermis also has dendritic cells (melanocytes and Langerhans cells) and neuroendocrine (Merkel) cells. Like every epithelium, the epidermis cells are renewed indefinitely thanks to a continuous mitotic activity.

Due to exposure to the environment, the skin is covered by a lipid layer from sebum and epidermal lipids. Sebum is an important skin factor, as it can be classified according to the amount of sebum secreted. In the cosmetic field, the facial skin is usually classified as dry, normal, combination or oily skin.

There is a cosmetic concern related to oily skin, that is, skin that produces a large amount of sebum. This is because such a condition modulates skin aspects such as: intense shine, sticky feeling, tendency to acne, pimples and blackheads and dilated and irregular pores.

Sebum is a lipid mixture comprising triglycerides, fatty acid esters, esterified waxes, squalene and cholesterol esters. Its main function is to protect the skin by controlling transpidermal water loss, forming a waterproof barrier.

The face has an average of three to nine hundred pilosebaceous follicles per square centimeter, however, several factors are involved in the regulation of the amount of sebum deposited on the skin surface, so what happens in the sebaceous gland should not be considered as the only cause of oiliness on the skin.

In people with oily skin, the sebaceous glands are hyperactivated, which can cause excessive shine and the presence of dilated pores. A consequence of dilated pores is an even more oily skin, with a greasy and shiny appearance.

A reduction in the pore diameter leads to a reduced amount of oil released and it further provides the skin with a healthier and blemish-free appearance.

Oiliness is still related to disturbances in the skin microbiota. This is because the microbiota has a variety of microorganisms that depend on the skin conditions. Where oiliness increases due to internal or external factors, the skin conditions favor bacteria that do not require oxygen to grow and use lipids instead. Such a population increases, reducing other bacterial populations that grow better in less oily environments. Thus, the inflammatory response that leads to the appearance of acne keeps the vicious circle of excessive oil and lipid-consuming bacteria, leaving the skin unbalanced.

Gram positive bacteria usually predominate in the skin, such as *Staphylococcus, Corynebacterium* and *Propionobacterium*. It interacts with other microbes, human cells and the immune system via different pathways that mediate the risk for diseases. Disturbances in this microbiota may influence the onset of diseases.

Moreover, certain types of skin require specific care, especially regarding hydration. Hydration is also an issue as it may compromise integrity of the skin.

DESCRIPTION OF RELATED ART

The state of the art describes a variety of cosmetic compositions. For example, WO12083906 relates to a method for providing a liquid cosmetic composition to be applied on the skin as a foam.

Document KR20180082050 discloses lentil extract, among other extracts, to control skin oiliness.

Document WO18122514 deals with a process that is intended to provide extracts of biological material for the extraction of active ingredients in general.

WO9619184 describes a composition for topical application comprising a topical vehicle, an irritating ingredient and an anti-irritant ingredient.

Accordingly, it is understood that in view of the relevant state of the art, there remains the need to provide cosmetic compositions to reduce and control oiliness of the skin in an immediate and prolonged manner while reducing the shine and pore size, masking visual imperfections and maintaining the skin hydration.

SUMMARY OF THE INVENTION

Thus, the present invention is intended to solve the technical issues of the state of the art by providing a topical cosmetic composition that significantly reduces and controls oiliness of the skin, as well as reduces the pore size, the skin shine, hydrates and masks optical imperfections therein. The composition further maintains the skin's natural and healthy microbiota.

In a first aspect, the present invention relates to a topical cosmetic composition in the form of a serum, which composition comprises: babassu starch, mandelic acid, a caprytoyl salicylic acid (LHA) (salicylic acid derivative) and *Lens esculenta* seed extract.

In a second aspect, the present invention relates to the use of the composition to reduce and control skin oiliness.

In a third aspect, the present invention relates to the use of the composition to reduce the average size of skin pores.

In a fourth aspect the present invention relates to the use of the composition to reduce the number of skin pores.

In a fifth aspect, the present invention relates to the use of the composition to reduce visual skin imperfections.

In a sixty aspect the present invention relates to the use of the composition to hydrate the skin.

Also, the inventive concept in common to all aspects of the invention is that they involve the composition of the first aspect.

From among the advantages of the present invention, in a non-exhaustive manner, is that it is able to:

restore the skin microbiota balance acting as a prebiotic;

control the skin oiliness throughout the day;

provide immediate reduction of shine and oiliness;

reduce skin oil production within 28 days;

reduce the pore sizes;

reduce the number of pores reduce oily skin imperfections, including acne marks;

hydrate and improve the skin texture.

These and other objects of the invention will be immediately valued by those skilled in the art and by companies with interest in the segment, and will be described in sufficient detail to be reproduced in the description below.

BRIEF DESCRIPTION OF THE FIGURES

In order to better define and clarify the present invention, the following figures are presented.

DETAILED DESCRIPTION OF THE INVENTION

Figure 1:
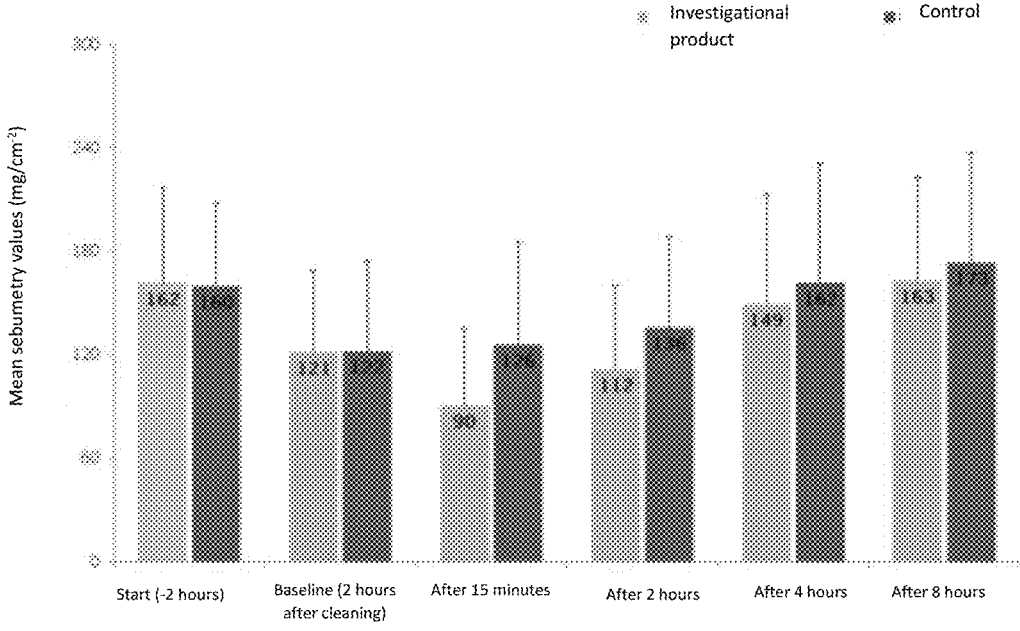
FIG. 1 graphically represents the mean values of sebaceous secretion obtained at the site of application of the serum of the present invention and at the control site.

The present invention describes a topical cosmetic composition and uses thereof in reducing and controlling oiliness, reducing pores, reducing visual skin imperfections, reducing shine, moisturizing and maintaining the skin's microbiota.

In the present invention, the term "maintenance of the skin microbiota" can also be understood as "preservation of the skin microbiota" or "microbiota balance", being defined as an ability to enable the presence of a natural and healthy skin microbiota. Furthermore, the term "skin microbiota" can also be understood as "skin flora".

In a first aspect, the present invention relates to a topical cosmetic composition in the form of a serum, which composition comprises: babassu starch, mandelic acid, a capryloyl salicylic acid (LHA) (salicylic acid derivative) and *Lens esculenta* seed extract.

A cosmetic serum is meant a cream gel with a light, refreshing and fast-absorbing texture. The serum of the present invention is ideal for combination and oily skin.

Among the ingredients required to provide the serum effects are babassu starch, mandelic acid, a capryloyl salicylic acid (LHA) (salicylic acid derivative) and *Lens esculenta* seed extract. Preferably, the composition comprises about 0.2 to 20% babassu starch, about 0.5 to 8% mandelic acid, about 0.1 to 2% LHA, about 2 to 10% *Lens esculenta* seed extract.

Mandelic acid is a high molecular weight alpha-hydroxy acid (2-hydroxy-2-phenylethanoic acid). Due to its high molecular weight, it is slowly absorbed by the skin, making a smoother exfoliation and stimulating cell renewal. On the skin, the compound improves the uneven texture of the skin resulting in an even appearance, in addition to leaving the skin softer and smoother.

Babassu starch is a biotechnological active ingredient of natural origin that can be found in ingredients such as: Babassu coconut mesocarp flour (*Orbignya phalerata*). The ingredient acts in the maintenance and balance of the skin's microorganisms. On the skin it reduces the appearance of acne and comedones.

*Lens esculenta* (lentil) seed extract is an active ingredient of natural origin that is rich in oligosaccharides. The ingredient provides increased keratinocyte differentiation by increasing transglutamase I and involucrin, causing a reduction in the number of nucleated cells around the pore. It further provides a decrease in sebum secretion and in pore sizes.

Capryloyl salicylic acid (LHA) is a lipohydroxy acid, a lipophilic derivative of salicylic acid (2-octanoyloxybenzoic acid). The ingredient is a keratolytic active that has good affinity to the epidermis, infiltrating the stratum corneum to make a precise, fine and specific microexfoliation. Moreover, the ingredient eliminates dead cells, unclogging pores and regulating excessive oil, hence reducing the number of lesions and the formation of comedones.

In one embodiment of the first aspect the invention further comprises cosmetically acceptable excipients. By cosmetically acceptable excipients is meant non-irritating and non-toxic substances, which are used to prepare and/or provide structure to a cosmetic form, and may or may not confer organoleptic properties on a composition such as, for example, color and odor, and may or may not provide a cosmetically desirable biological effect such as hydration. The cosmetically acceptable excipients of the present invention can be formulated in different amounts, depending on the type of characteristics envisioned in the final cosmetic product.

The cosmetically acceptable excipients in accordance with the present invention may be those known to the person skilled in the art, such as those cited in the "International Cosmetic Ingredient Dictionary & Handbook", 16th Edition.

In a particular embodiment, the cosmetically acceptable excipients of the present invention can be, in a non-exhaustive manner, those belonging to the classes of solvents, emollients, absorbents, emulsifiers, opacifiers, skin conditioners, preservatives, viscosity controllers, skin protectors, denaturants, perfumes, moisturizers, antioxidants, emulsion stabilizers, plasticizers, chelating agents, dyes and buffers.

Preferably, the solvent may comprise water, alcohol or a mixture thereof; the emollient may comprise glycerin, dicaprilyl carbonate or a mixture thereof; the absorbent may comprise tapioca starch; the skin conditioner may comprise pentylene glycol; the emulsifier/stabilizer may comprise arachidyl alcohol, sodium acrylate copolymer, xanthan gum, or a mixture thereof.

The serum of the present invention can be made by any process known to the person skilled in the art.

The present invention differs in many ways from the state of the art. For example, the preferred embodiment of the present invention is a polymeric emulsion, which is technically difficult to obtain due to mandelic acid instability. Moreover, the present invention exhibits an immediate (about 15 minutes after application of the product) and prolonged effect of reducing and controlling skin oiliness. The effect of reducing skin oiliness after 28 days of use of the product, among other effects, should be highlighted, as shown in the examples and figures.

The combination of the ingredients of the first object provide the technical effects of the present invention. For example, an improvement in the reduction and control of oiliness, reduction in the size and amount of pores, improvement in skin uniformity (it masks the visual imperfections of the skin) and hydration.

Regarding the control and reduction of oiliness, the invention acts via 8 mechanisms, namely: (1) increase in keratinocyte maturation to accelerate cell turnover; (2) decreased in production of sebum; (3) collagen stimulation to reduce the pore size; (4) decrease in the adhesion of superficial skin cells; (5) skin cell renewal; (6) rebalance of the skin's microorganisms; (7) increase in skin hydration; (8) an astringent effect.

The technique for assessing the reduction and control of oiliness is sebumetry, which has the benefit of being a non-invasive methodology that evaluates the sebaceous lipid secretion profile on the skin surface along a kinetics conceived as short or long.

Thus, in a second aspect, the present invention relates to the use of the composition of the first aspect to reduce and control skin oiliness.

In one embodiment the second aspect of the invention relates to an immediate reduction and control of skin oiliness.

By immediate is meant the time elapsed of about 15 minutes after application of the composition of the first aspect.

In another embodiment the second aspect of the invention relates to a prolonged reduction and control of skin oiliness.

In another embodiment the second aspect refers to the reduction and control of oiliness after 14 and 28 days of application of the product.

The effect of reducing the size/number of pores was achieved by a non-invasive methodology designated as image analysis, which evaluates the morphology and topographic characterization of the skin surface.

By the cited methodology, it was noticed that 7 days after application of the product, there was a reduction in the pore size by up to 4.2% and in the number of pores by up to 5%. The pores were also less visible by up to 78%.

In 14 days there was a reduction in the pore size by up to 5.0% and in the number of pores by up to 7.3%. In addition, the pores are less visible by up to 78%.

In 28 days there was a reduction in the pore size of up to 5.7%, pores were less apparent by up to 78%.

Thus, in a third aspect the present invention relates to the use of the composition to reduce the average pore size of the skin.

In one embodiment of the third aspect the invention relates to a reduction in the average pore size after 28 days.

Furthermore, in a fourth aspect the present invention relates to the use of the composition to reduce the number of skin pores.

Skin imperfections were assessed using an objective non-invasive methodology designated as image analysis, which assessed skin tone uniformity after continuous use of the composition of the first aspect. The methodology shows that the composition reduces acneic skin imperfections, reduces imperfections, provides a more uniform skin with less signs of imperfections.

Thus, in a fifth aspect the present invention relates to the use of the composition to reduce visual skin imperfections.

In one embodiment of the fifth aspect the present invention reduces visual skin imperfections after 30 days of use of the composition of the first aspect.

Moreover, the present invention further provides skin hydration. Hydration was assessed through an objective non-invasive methodology designated as corneometry, which evaluates the amount of water aggregated to the skin surface after use of the product by evaluating the change in capacitance caused by such water build up.

In a sixty aspect the present invention relates to the use of the composition to hydrate the skin.

In one embodiment of the sixth aspect the invention immediately hydrates the skin.

In another embodiment the invention hydrates the skin in a prolonged manner within up to 24 hours.

The serum of the present invention is applied to the skin in order to form an even layer of the product on the previously clean and dry face.

EXAMPLES—EMBODIMENTS

The examples shown herein are intended only to exemplify one of the numerous ways of carrying out the invention, without limiting its scope.

For the purpose of illustrating the technical effects of the present invention, and not to limit it, whenever the examples refer to an "investigational product" reference will be made to a topical cosmetic composition in the form of a serum, which is a preferred embodiment of the composition of the first aspect. The composition of the "investigational product" can be found in table 1.

TABLE 1

| Composition of the investigational product (serum) | |
| --- | --- |
| Ingredient | Concentration (% w/w) |
| Water | 65.89 |
| Ethyl alcohol | 8.00 |
| Glycerin | 4.00 |
| Dicaprylyl Carbonate | 4.00 |
| Tapioca Starch | 4.00 |
| Pentylene glycol | 3.00 |
| Lens esculenta seed extract | 3.00 |
| Arachidyl alcohol | 2.20 |
| Sodium acrylate copolymer | 2.00 |
| Mandelic Acid | 2.00 |
| Babassu coconut mesocarp flour (Orbignya phalerata | 0.50 |
| Capryloyl salicylic acid | 0.50 |
| Sodium Hydroxide Flake | 0.30 |
| Perfume | 0.30 |
| Xanthan Gum | 0.20 |
| Sodium Glycolate | 0.10 |
| Conobea scoparioides leaf oil | 0.01 |

Example 1—Effect of the Investigational Product on the Reduction and Control of Facial Skin Oiliness after Application of a Cosmetic Product Objective This example is intended to demonstrate the effect of the investigational product on the reduction and control of skin oiliness at 15 minutes, 2, 4 and 8 hours after application.

Methodology

Twenty participants with a mean age of 43±8 were included. Among the participants, the phototype (Fitzpatrick) distribution was as follows: 5% phototype II, 55% phototype III and 40% phototype IV. Participants were instructed to discontinue the use of any cosmetic products on the face 7 days prior to the start of the study.

In the frontal region (forehead) of the participants, two sites were marked (areas measuring 2.5 cm×4.0 cm). After 30 minutes of the participant staying in an air-conditioned environment, the initial data on oiliness was obtained at the marked sites.

Then, the procedure of cleaning the sites with water and neutral soap was performed. After 2 hours of cleaning, new measurements of skin oiliness were performed to collect baseline oiliness values. After these 2 hours the investigational product was applied and new measurements of skin oiliness were obtained after 15 minutes, 2, 4 and 8 hours of application of the product.

Twenty microliters of the investigational product were applied to the participants by spreading it evenly over the site with the aid of a disposable finger. At the control site no product was applied.

Measurements were made by placing a probe to measure the oil content by means of a photometric method (using Cassette Sebumeter SM810), keeping the pressure constant for 30 seconds. Reduction in skin oiliness is evidenced by the decreased amount of sebaceous secretion, the lower the value, the greater the reduction in oiliness, and the longer this reduction lasts, the greater the control of oiliness provided.

Results

As a result, the investigational product was shown to provide a significant reduction in facial skin oiliness after 15 minutes and 2 hours of application, as compared to the control. It indicated that the investigational product controlled facial skin oiliness for up to 2 hours.

The investigational product was shown to provide a significant mean reduction in facial skin oiliness relative to the baseline condition of 25.6% after 15 minutes of application.

The graph in FIG. 1 illustrates the values found in example 1.

Example 2—Effect of the Investigational Product on the Reduction and Control of Oiliness This example is intended to demonstrate the effectiveness in reducing and controlling facial skin oil after application of the investigational product.

Methodology

Twenty-two participants with a mean age of 38±12 were included. Among the participants, the phototype (Fitzpatrick) distribution was as follows: 91% phototype III and 9% phototype IV. Participants were instructed to discontinue the use of any cosmetic products on the face 7 days prior to the start of the study.

In the frontal region (forehead) of the participants, two sites were marked (areas measuring 2.5 cm×4.0 cm). After 30 minutes of the participant staying in an air-conditioned environment, the initial data on oiliness was obtained at the marked sites.

Then, the procedure of cleaning the sites with water and neutral soap was performed. After 2 hours of cleaning, new measurements of skin oiliness were performed to collect baseline oiliness values. After these 2 hours the investigational product was applied and new measurements of skin oiliness were obtained after 30 minutes, 2, 4 and 8 hours of application of the product.

The same evaluation procedure was performed on the first day of the study (T1) and after 3 days (T3) of home use of the investigational product.

There was an investigation of the action of the product in the reduction and control of oiliness at T1 and after 7 days and 14 days of home use of the investigational product.

Twenty microliters of the investigational product were applied to the participants by spreading it evenly over the site with the aid of a disposable finger. At the control site no product was applied.

Measurements were made by placing a probe to measure the oil content by means of a photometric method (using Cassette Sebumeter SM810), keeping the pressure constant for 30 seconds. Reduction in skin oiliness is evidenced by the decreased amount of sebaceous secretion, the lower the value, the greater the reduction in oiliness, and the longer this reduction lasts, the greater the control of oiliness provided.

Results

Figure 2:
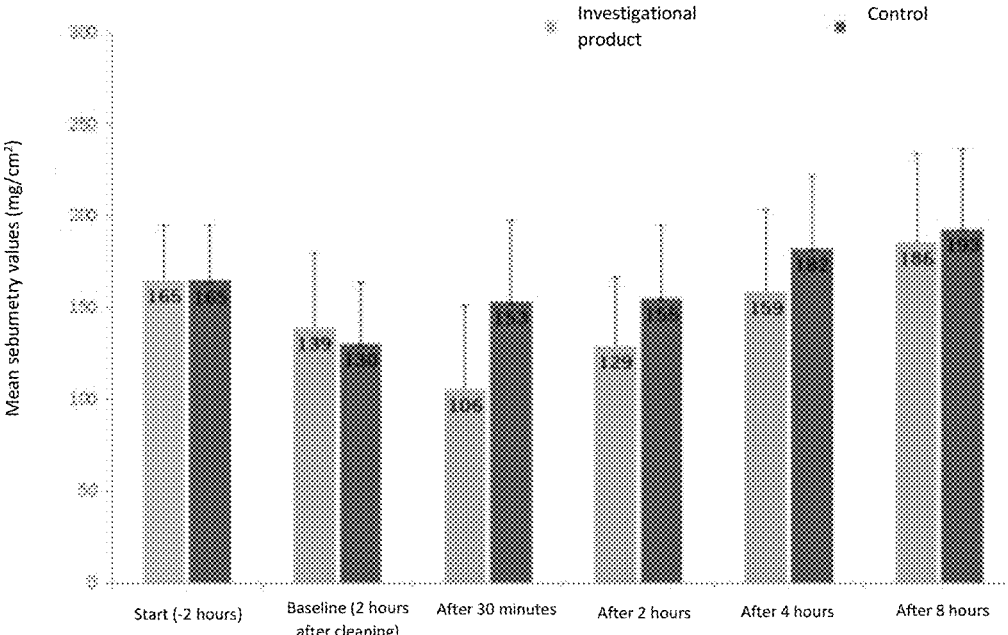
FIG. 2 graphically represents the mean values of sebaceous secretion obtained at the site of application of the serum of the present application and at the control site on the first evaluation day (T1).

On the first day of the study (T1) the investigational product was shown to provide a significant mean reduction in facial skin oiliness of 24.2% after 30 minutes of application relative to the baseline condition. Furthermore, there was a significant reduction in facial skin oiliness after 2 and 4 hours of application relative to the control. These facts indicated that the investigational product controlled facial skin oiliness for up to 4 hours. FIG. 2 shows the values discussed here.

Figure 3:
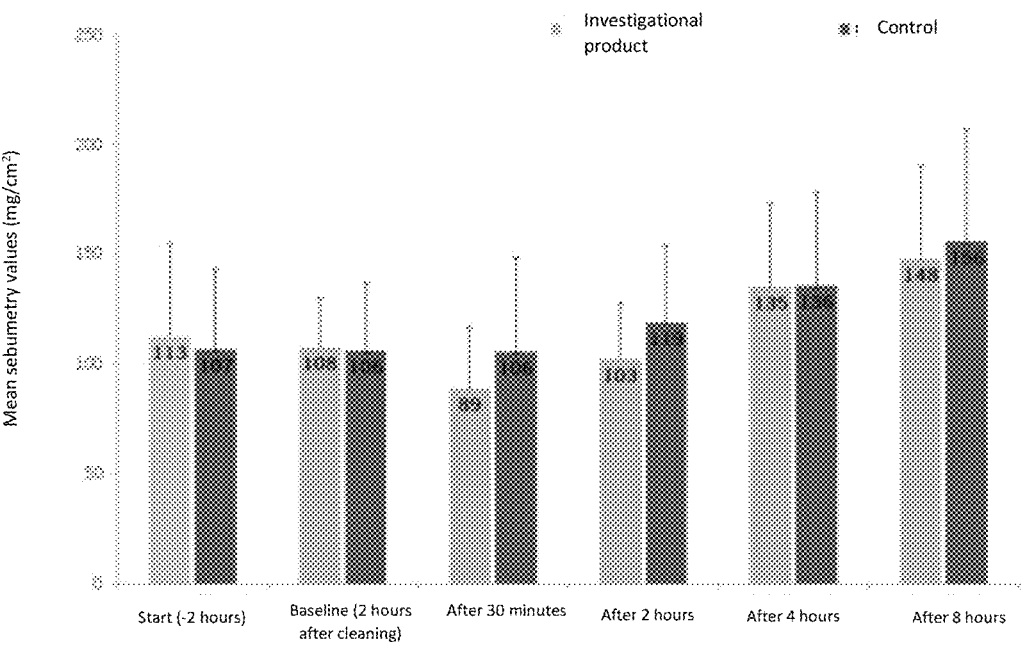
FIG. 3 graphically represents the mean values of sebaceous secretion obtained at the site of application of the serum of the present application and at the control site after 3 days of home use in the third evaluation day (T3).

After 3 days of use at home a significant mean reduction in facial skin oiliness of 17.4% was observed after 30 minutes of application in relation to the baseline condition. Furthetmore, there was also a significant reduction in facial skin oiliness after 2 hours of application relative to the control. It indicated that the investigational product controlled facial skin oiliness for up to 2 hours. FIG. 3 shows the values discussed here.

Figure 4:
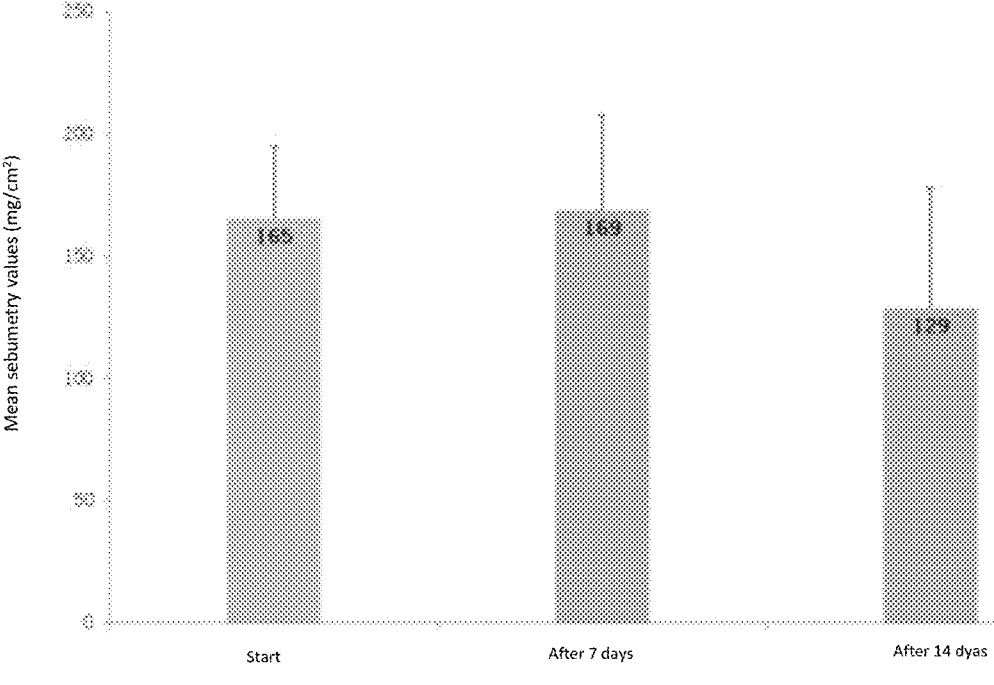
FIG. 4 graphically represents the mean values of sebaceous secretion obtained throughout the study to assess reduction of facial skin oiliness after 7 and 14 days of home use of the serum of the present invention.

There was a significant reduction in facial skin oiliness after 14 days of home use of the investigational product, the reduction was 22.0%. FIG. 4 shows the values discussed here.

Example 3—Effect of the Investigational Product on the Reduction of Facial Skin Oiliness After 28 Days of Home Use Objective The instant example is intended to demonstrate the reduction in facial skin oiliness after 28 days of home use of the investigational product.

Methodology

Twenty-three participants with a mean age of $41\pm10$ were selected. Among the participants, the phototype (Fitzpatrick) distribution was as follows: 4% phototype II, 61% phototype III and 35% phototype IV. Participants were instructed to discontinue the use of any cosmetic products on the face 7 days prior to the start of the study.

In the frontal region (forehead) of the participants, two sites were marked (areas measuring 2.5 cm×4.0 cm). The measurements performed in this study were obtained after the participants remained for 30 minutes in a controlled, air-conditioned environment.

Participants were instructed to apply small amounts of the product on the previously cleansed and dried face, once a day, at night.

Results

Figure 5:
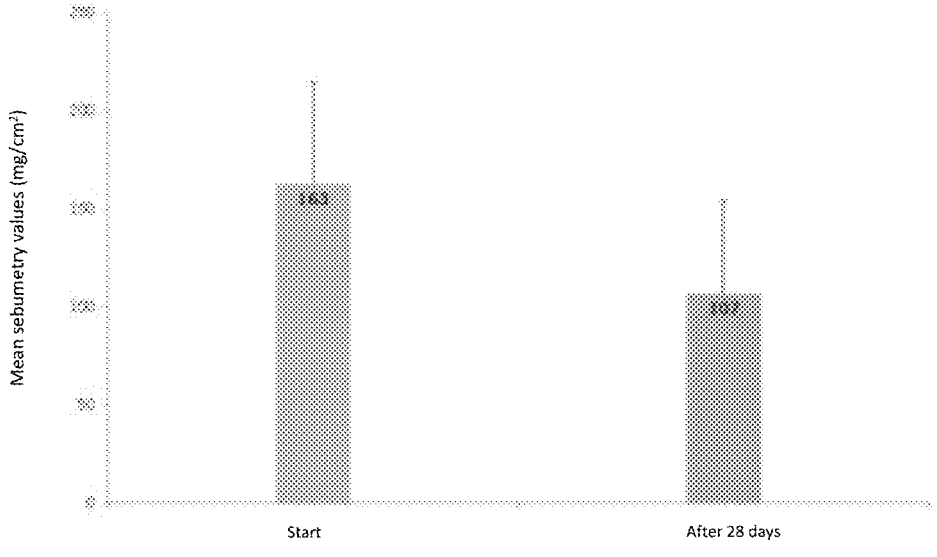
FIG. 5 depicts sebaceous secretion values obtained after 28 days of use of the serum of the present invention.

There was a significant reduction in facial skin oiliness after 28 days of home use of the investigational product. As shown in FIG. 5, there was a significant mean reduction in facial skin oiliness of 34.5% after 28 days of home use.

Example 4—Effects of the Investigational Product on the Reduction of Facial Skin Pore Size by Image Analysis Objective This example is intended to demonstrate the effect of the investigational product on the issue of the reduction in pore size after 15 minutes, 2, 4 and 8 hours of application of the product.

Methodology

Twenty participants with a mean age of $43\pm8$ were included. Among the participants, the phototype (Fitzpatrick) distribution was as follows: 5% phototype II, 55% phototype III and 40% phototype IV. Participants were instructed to discontinue the use of any cosmetic products on the face 72 hours prior to the start of the study. There were no reports or evidence of adverse reactions during the study.

The methodology consisted of assessing the reduction in the average size and number of pores in the facial skin of the research participants through image analysis.

The results achieved are a comparison between high resolution photographic images under controlled and standardized conditions. Data were obtained at an initial time (prior to application of the product) and 15 minutes, 2, 4 and 8 hours after application of the serum.

According to each volunteer's face morphology, a selection area was determined for analysis of the apparent pore average size. Analysis was kept constant for each participant in terms of size and placement between the evaluation conditions, thus allowing a comparison to be made between the images.

Figure 7:
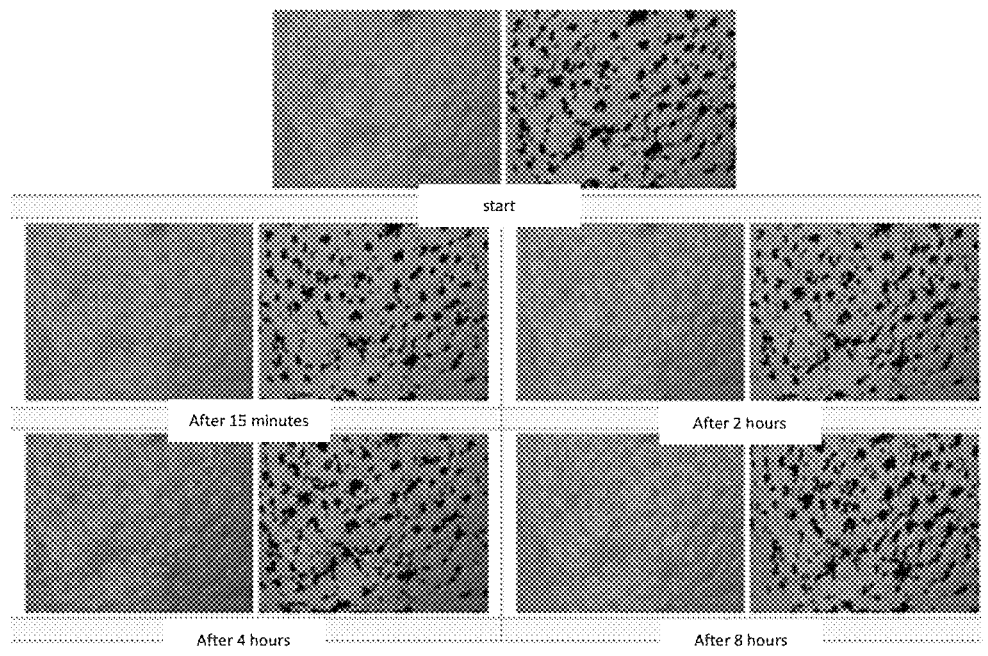
FIG. 7 represents examples of images obtained for one of the research participants at the beginning of the study, after 15 minutes 2, 4 and 8 hours of application of the serum of the present invention.

The selected areas were assessed using a particle morphology analysis tool, which identifies, isolates and analyzes via color contrasting information the geometric parameters of the detected visible pores, as shown in FIG. 7.

Results

Figure 6:
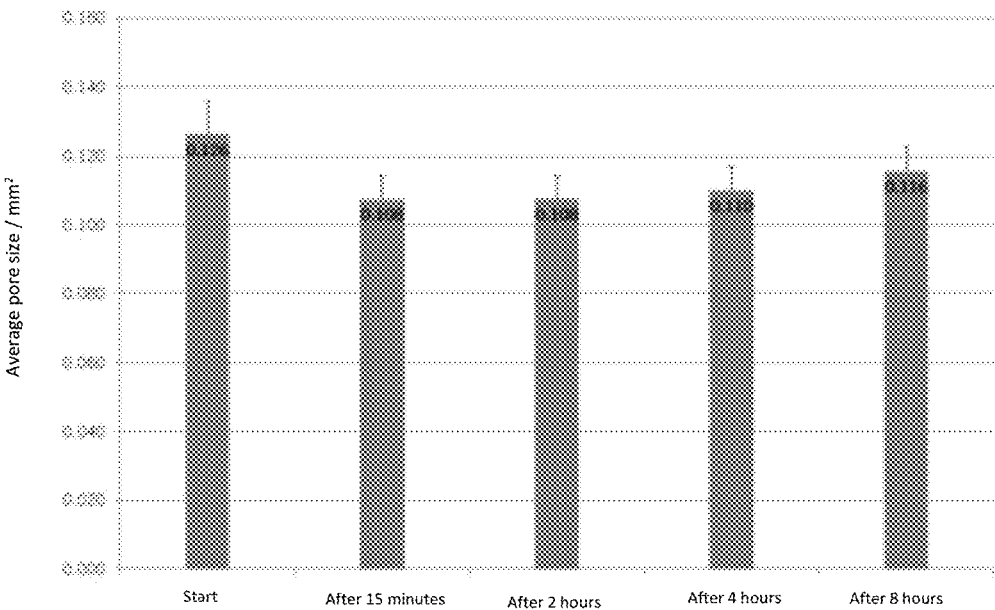
FIG. 6 graphically represents the average values of the average pore sizes of the research participants after 15 minutes, 2, 4 and 8 hours of application of the serum of the present invention.

After 15 minutes of application of the investigational product, there was a significant reduction in the average pore size of 7.8%, reaching up to 11.9%. After 2 hours of application of the investigational product, there was a significant reduction in the average pore size of 5.5%, reaching up to 8.2%. After 4 hours of application of the investigational product, there was a significant reduction in the average pore size of 5.5, reaching up to 8.2%. After 8 hours of application of the investigational product, there was no significant difference in the average pore size relative to the baseline condition (before application of the product). FIG. 6 graphically illustrates the study results.

Figure 8:
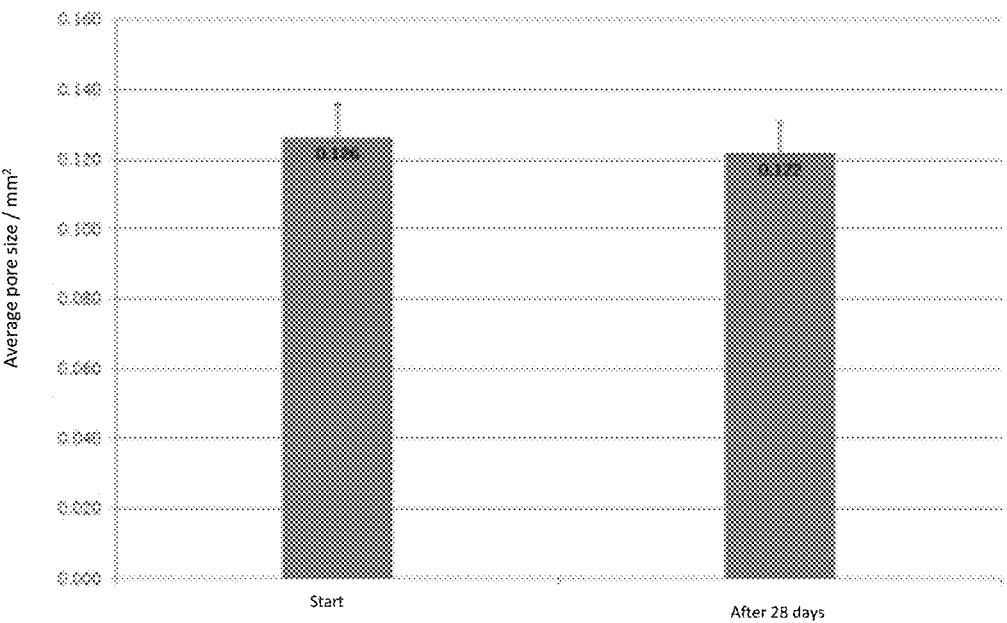
FIG. 8 represents the average values of the average pore sizes of the research participants at the beginning of the study and after 28 days of home use of the serum of the present invention.
Figure 9:
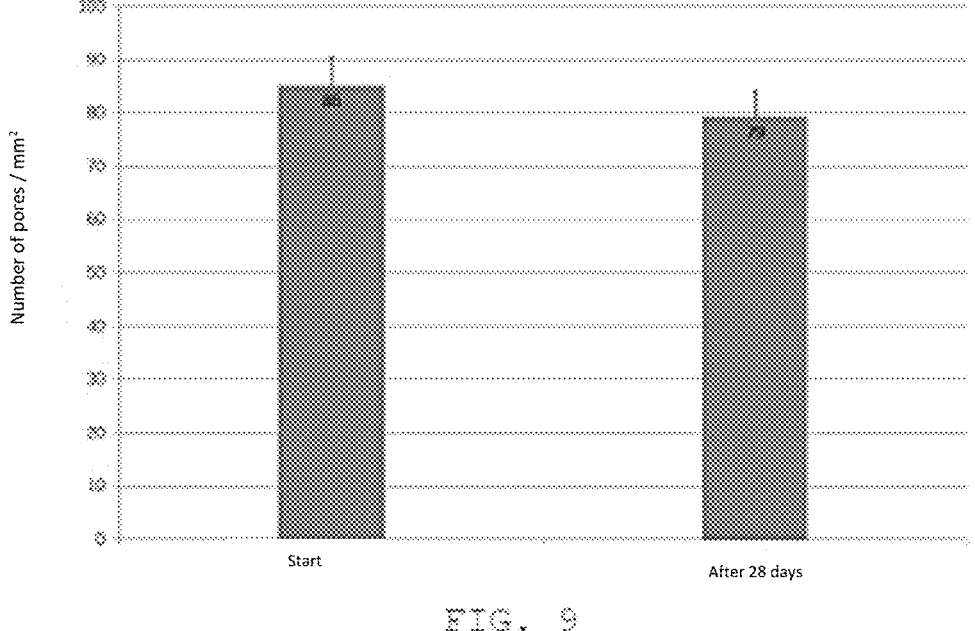
FIG. 9 represents the average values of the number of pores of the research participants at the beginning of the study and after 28 days of home use of the serum of the present invention.
Figure 10:
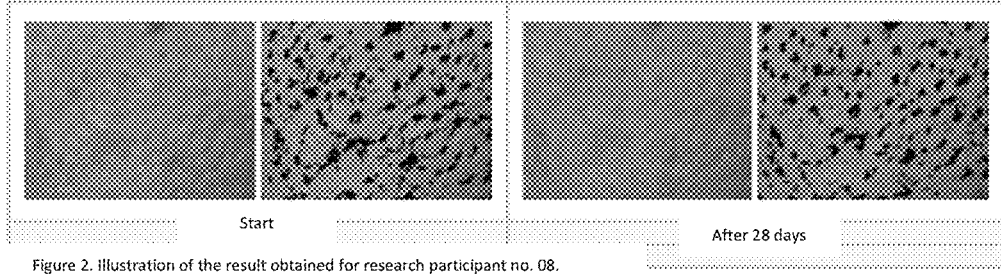
FIG. 10 shows an example of images obtained for one of the research participants after 28 days of home use of the serum of the present invention.

Moreover, use of the product for 28 days was shown to lead to a significant reduction in the average pore size of 3.4%, reaching up to 5.7% and a significant reduction in the number of pores of 6.4%, reaching up to 8.8%. FIGS. 8, 9 and 10 illustrate the results achieved after 28 days of home use.

Example 5—Effect of the Investigational Product in Masking Imperfections

For the study, 11 participants were selected with a mean age of $30\pm10$ years. 9% of the participants are phototype II (Fitzpatrick) and 82% are phototype III. The participants were instructed to discontinue the use of any topical product 48 hours prior to the start of the study.

The methodology consisted of the objective analysis performed by obtaining photographic images of the face of the research participants at the beginning of the study and after 30 days of home use of the investigational product.

Results

Figure 11:
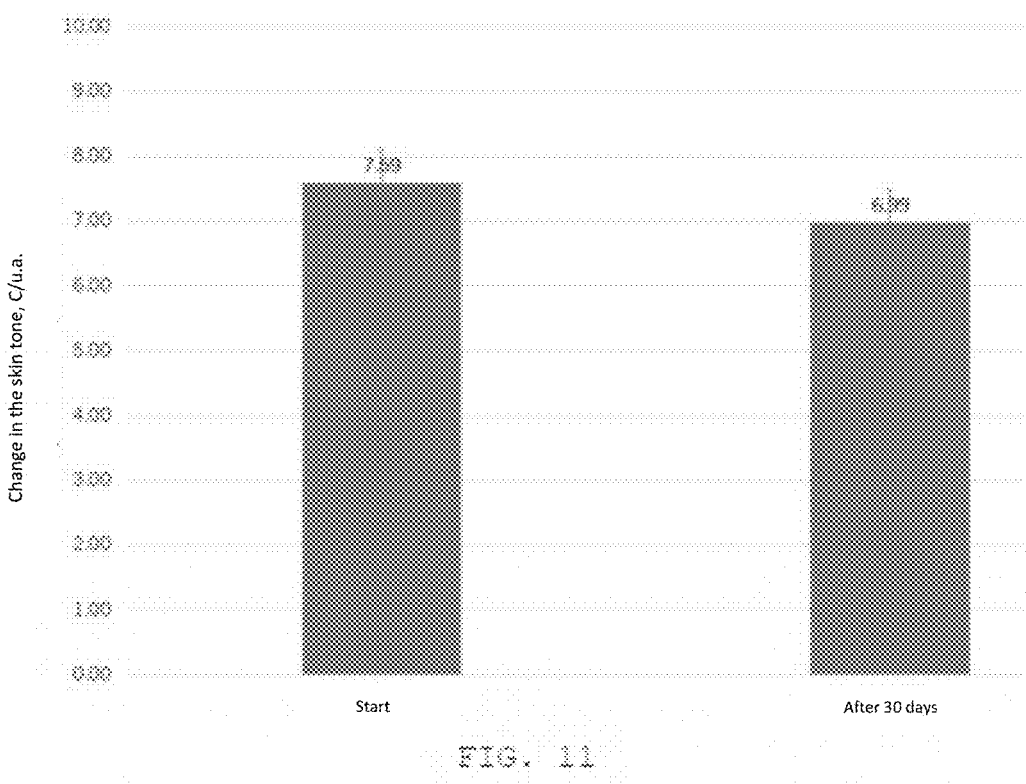
FIG. 11 represents the average values obtained from the initial skin color variation and after 30 days of use of the serum of the present invention.

As a result, after 30 days of use of the investigational product the skin color was found to be 7.9% more homogeneous, reaching up to 10.70%. Also, 100% of the research participants showed improved skin color homogenization after 30 days of use of the investigational product. Therefore, the product masked facial skin imperfections. FIG. 11 shows the results graphically.

Example 6—Effect of the Investigational Product on Skin Hydration by Corneometry For the study, 20 participants were selected with a mean age of $44\pm6$ years. 60% of the participants are phototype III (Fitzpatrick) and 40% are phototype IV. The participants were instructed to discontinue the use of any topical product 48 hours prior to the start of the study.

The methodology consisted of keeping the participants for 30 minutes in an air-conditioned environment, so that the baseline measurements (prior to the application of the investigational product) of skin capacitance at the marked sites were obtained. Thereafter, 20 microliters of the investigational product were applied. After application, new capacitance measurements were obtained after 15 minutes, 4 and 8 hours of application. After 8 hours, the research participants went back home, being instructed not to wet or wash their arms. The following day, they returned to the laboratory for a measurement be taken 24 hours of the application.

Figure 12:
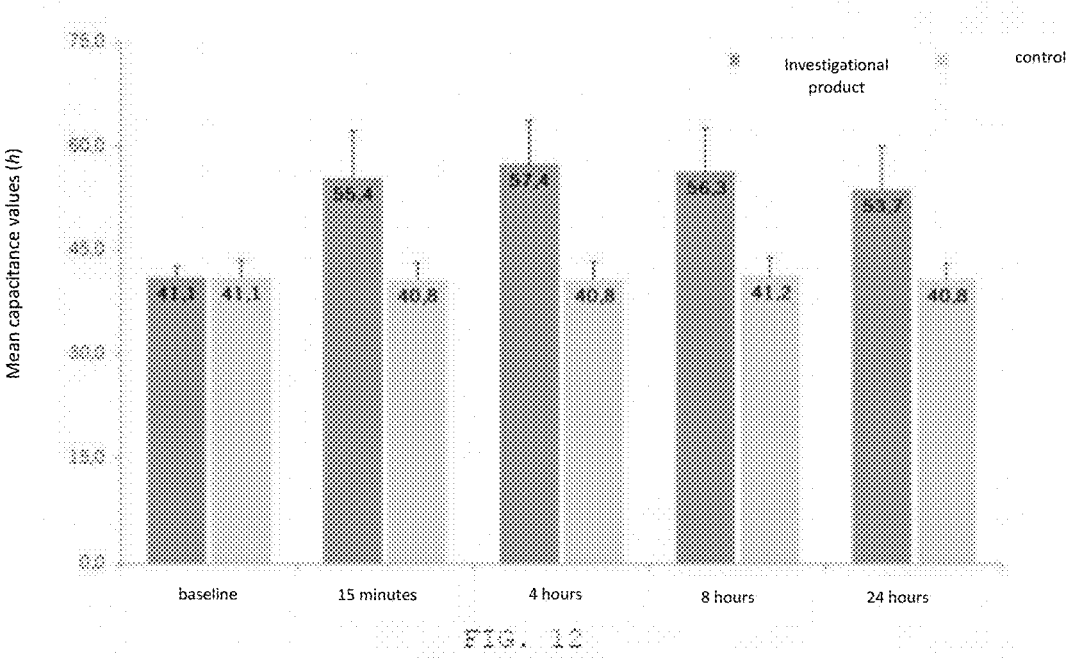
FIGS. 12 and 13 show the mean capacitance values (h) and the percentage of increase in skin hydration (% H) obtained throughout the study, respectively.
Figure 13:
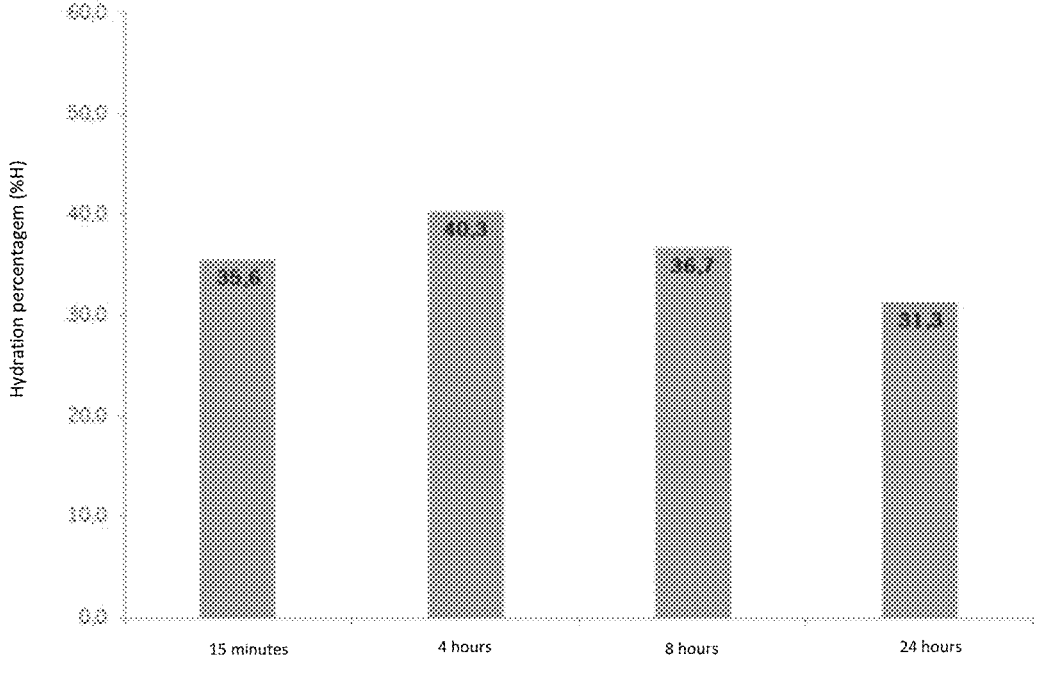

The study concluded that the investigational product conferred a significant increase in skin hydration after 15 minutes, 4, 8 and 24 hours of application, as compared to the control. The investigational product kept the skin hydrated for up to 24 hours after application. The investigational product increased the skin hydration level by up to 40.3%. FIGS. 12 and 13 illustrate the results discussed herein.

Also, 100% of the survey participants have shown improved skin hydration after treatment with the investigational product.

Those skilled in the art will value the knowledge presented herein and may reproduce the invention in the disclosed embodiments and other variants, as covered by the scope of the appended claims.

Example 7—Evaluation of the Investigational
Product in the Maintenance of the Skin Microbiota
by Reducing Porphyrins Conclusion of the imaging study was that after 28 days of use of the investigational product on the facial region, the amount of porphyrin is reduced significantly, in particular in the region with the highest oil production (nose), which demonstrates effect of the product in reducing the amount of bacteria that consume the skin sebum and secrete porphyrin.

The invention claimed is:

1. A topical cosmetic composition characterized by comprising 0.2 to 20 wt % babassu starch, 0.5 to 8 wt % mandelic acid, 0.1 to 2 wt % capryloyl salicylic acid, 2 to 10 wt % *Lens esculenta* seed extract, dicaprylyl carbonate, and tapioca starch, wherein the weight percentages are calculated based on the total weight of the composition.

2. The composition according to claim 1, characterized in that it contains cosmetically acceptable excipients selected from the class of: solvents, emollients, absorbents, emulsifiers, opacifiers, skin conditioners, preservatives, viscosity controllers, skin protectors, denaturing agents, perfumers, moisturizers, antioxidants, emulsion stabilizers, plasticizers, chelating agents, dyes or buffers.

3. The composition according to claim 1, characterized in that it is an emulsion.

4. A method of reducing and controlling skin oiliness, said method comprising applying the composition as defined in claim 1 to skin daily.

5. The method according to claim 4, characterized in that it is to reduce and control the skin oiliness about 15 minutes after application of the composition.

6. The method according to claim 4, characterized in that it is to reduce and control skin oiliness after 14 days of applying the composition.

7. A method of reducing average skin pore size, said method comprising applying the composition as defined in claim 1 to skin daily.

8. The method according to claim 7, characterized in that it is to reduce the average skin pore size after 28 days of applying the composition.

9. A method of reducing the number of skin pores, said method comprising applying the composition as defined in claim 1 to skin daily.

10. A method of reducing visual skin imperfections, said method comprising applying the composition as defined in claim 1 to skin daily.

11. The method according to claim 10, characterized in that it reduces visual skin imperfections after 30 days of applying the composition.

12. A method of hydrating skin, said method comprising applying the composition as defined in claim 1 to skin daily.

13. The method according to claim 12, characterized in that it is to hydrate the skin about 15 minutes after application of the composition.

14. The method according to claim 12, characterized in that it hydrates the skin after 30 days of applying the composition.

15. A method of maintaining and controlling the skin microbiota, said method comprising applying the composition as defined in claim 1 to skin daily, characterized in that it is to maintain and control the skin microbiota.

16. A method of reducing the number of porphyrins on facial skin, said method comprising applying the composition, as defined in claim 1, to facial skin daily, characterized in that the method reduces the number of porphyrins on the facial skin after 28 days of applying the composition.

17. A serum for facial application, characterized in that it comprises the composition as defined in claim 1.

* * * * *